United States Patent [19]

Steen et al.

[11] Patent Number: 5,185,265
[45] Date of Patent: Feb. 9, 1993

[54] PULSE MODULATION OF THE EXCITATION LIGHT SOURCE OF FLOW CYTOMETERS

[75] Inventors: Harald B. Steen; Otto Sorensen, both of Oslo, Norway

[73] Assignee: Skatron A/S, Tranby, Norway

[21] Appl. No.: 616,938

[22] Filed: Nov. 21, 1990

[30] Foreign Application Priority Data

Nov. 24, 1989 [NO] Norway .................................. 894680

[51] Int. Cl.$^5$ ............................................. G01N 21/17
[52] U.S. Cl. ........................................ 436/63; 436/172; 356/39; 356/72; 356/73; 356/336; 250/459.1
[58] Field of Search ................ 436/63, 172; 356/39, 356/336, 72, 73; 250/459.1, 222.2, 461.2

[56] References Cited

U.S. PATENT DOCUMENTS

| | | | |
|---|---|---|---|
| 4,198,567 | 4/1980 | Eneroth et al. | 250/459.1 |
| 4,284,355 | 8/1981 | Hansen et al. | 356/335 |
| 4,737,025 | 4/1988 | Steen | 356/39 |
| 4,778,593 | 10/1988 | Yamashita et al. | 356/39 X |
| 4,786,165 | 11/1988 | Yamamoto et al. | 356/39 X |
| 4,986,657 | 1/1991 | Ohe | 250/222.2 |

Primary Examiner—James C. Housel
Assistant Examiner—Jeffrey R. Snay
Attorney, Agent, or Firm—Cushman, Darby & Cushman

[57] ABSTRACT

A method for increasing the intensity of the excitation light, and thereby the sensitivity, of flow cytometers. The initial part of the signal produced by each cell as it enters the excitation focus triggers a current pulse to the excitation light source, with a duration approximately similar to the time required for the cell to pass through the focus. This current pulse, which is superimposed on the constant operating current to the light source, causes an increase of the intensity of the excitation light during the period when the cell is passing through the excitation focus and thereby an increase of the sensitivity of the flow cytometer.

6 Claims, 2 Drawing Sheets

PULSE MODULATION OF THE EXCITATION LIGHT SOURCE OF FLOW CYTOMETERS

BACKGROUND OF THE INVENTION

A flow cytometer is an instrument for measuring the fluorescence and light-scattering of biological cells and other microscopical particles. Carried by a laminar flow of water with a cross-section of the order of 100 µm, the cells pass one-by-one through the focus of an intense source of excitation light. As a cell passes through this focus, it emits a short pulse of fluorescence as well as a pulse of scattered light. Thus, one can measure the cellular content of a constituent, such as DNA, which has been labelled with a fluorescent dye, as well as its size, which is determined from the light-scattering intensity. The excitation light source can be a continuous wave (cw) laser or some other high intensity light source having a constant intensity, such as a high pressure arc lamp containing either mercury or xenon. By means of dichroic mirrors, the fluorescence can be split into different spectral components which are measured by separate detectors. The scattered light may be measured by separate detectors at different scattering angles to provide information, not only on cell size, but also on structural features of the cells.

The fluorescence sensitivity, or fluorescence detection limit, of a flow cytometer is defined as the smallest amount of fluorescent material per cell that can be detected by the instrument. Likewise, the light-scattering sensitivity, or light-scattering detection limit, is defined as the smallest cell of a given composition that can be detected. The detection limit is determined by the size of the signal, as well as of the level of background, or noise, on which the signal is superimposed. This noise has two principally different sources: a) electrical noise from the electronics used to amplify and transmit the pulses from the light detectors, and b) optical noise which is due to the constant background of light caused by imperfect filters and fluorescence from lenses and other optical components. Whereas the electrical noise in flow cytometers can be reduced to an insignificant level, there is a principal limit to the optical noise. Thus, even if the power consumption of a light source is perfectly constant, the number of photons, n, emitted within a given period of time will fluctuate with a standard deviation, s, given by Equation 1:

$$s = n^{\frac{1}{2}} \quad (1)$$

and the relative standard variation, cv, in the measurement of s is given by Equation 2:

$$s = n^{-\frac{1}{2}} \quad (2)$$

This fluctuation of the light intensity, which we shall denote "optical noise", is a consequence of the stochastic nature of the process of light emission and is true for all light sources, including the fluorescent cell and the various sources of optical background in the flow cytometer. The optical noise thus puts a principal limit to any measurement of light intensity. Only by increasing n, that is either by increasing the light intensity or by increasing the observation period, can this limit be reduced. In the flow cytometer the observation period is limited by the passage time of the cell through the excitation focus.

Since the signal increases in proportion to the excitation intensity, while the optical noise, according to Equation 1, increases in proportion to the square root of the intensity, the signal-to-noise ratio will increase in proportion to the square root of the excitation intensity, and the detection limit will decrease in the same proportion.

SUMMARY OF THE INVENTION

The present invention provides a method for increasing the excitation intensity in flow cytometers and thereby for increasing the sensitivity and reduce the detection limit. The method according to the invention is characterized in that the signal produced by a cell entering the excitation focus of a flow cytometer triggers a pulse of electrical power from a secondary power source to the excitation light source, to transiently increase the excitation intensity during the time the cell passes through the excitation focus, and thereby produce an increase of the measuring sensitivity of the flow cytometer.

BRIEF DESCRIPTION OF THE DRAWINGS

Further details of the invention will appear from the description below with reference to the enclosed drawing figures illustrating a preferred, non-limitative embodiment of the invention.

In the drawings.

DETAILED DESCRIPTION

Figure 1:
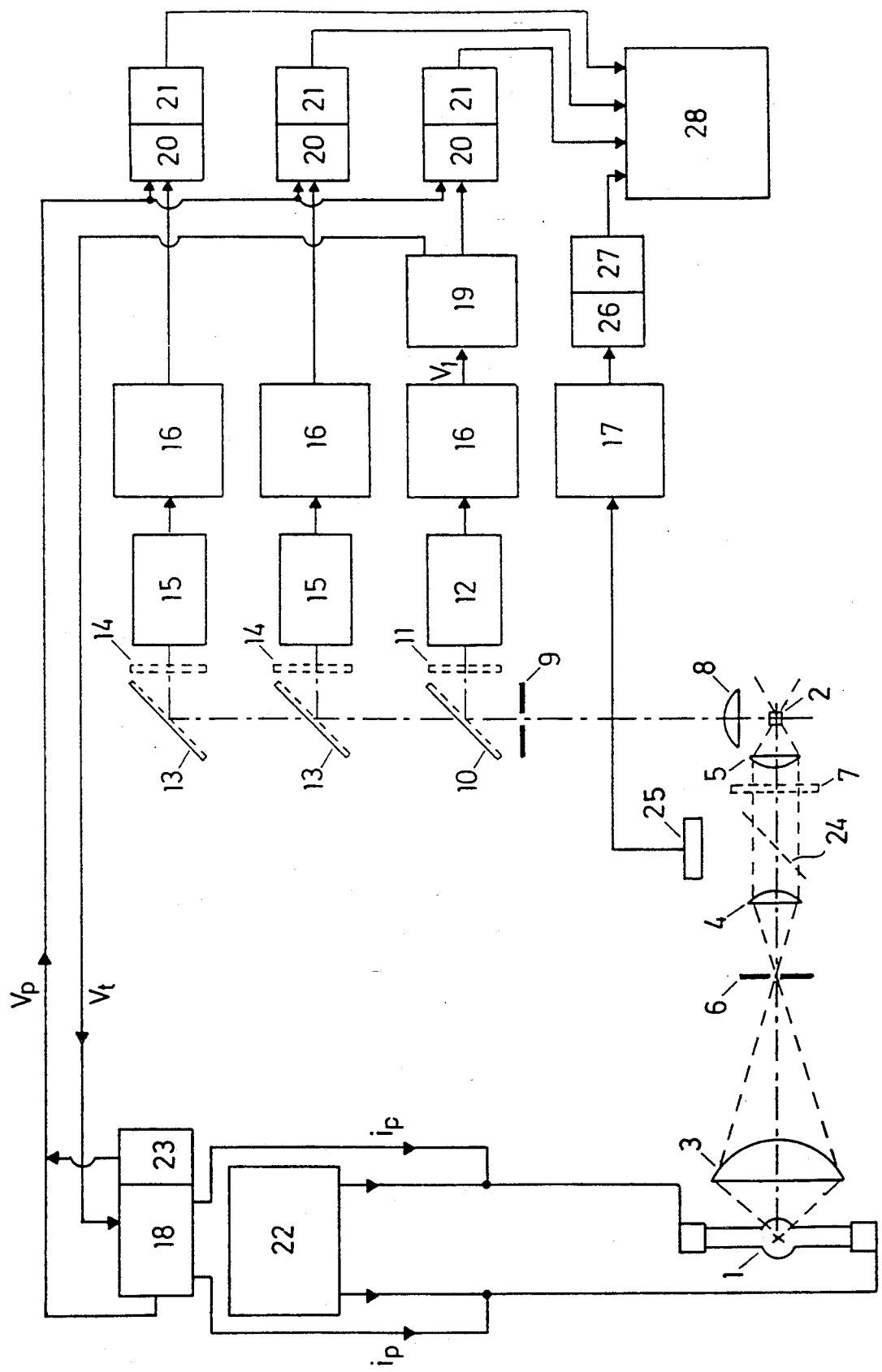
FIG. 1 illustrates the flow cytometer device utilized with the method according to the invention.
Figure 2A:
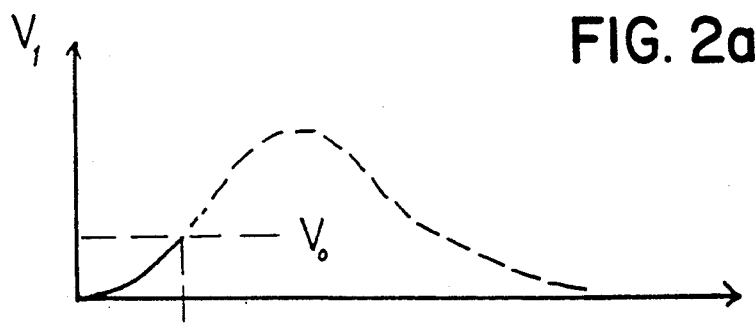
FIGS. 2a–e illustrate typical signal wave forms of the flow cytometer device.
Figure 2B:
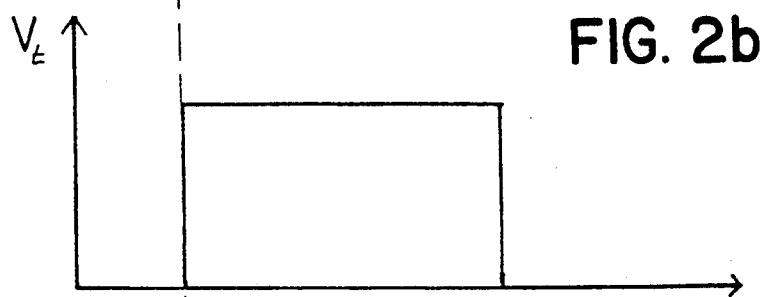
Figure 2C:
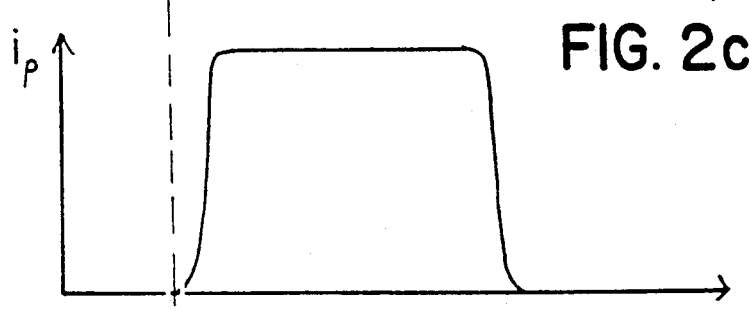
Figure 2D:
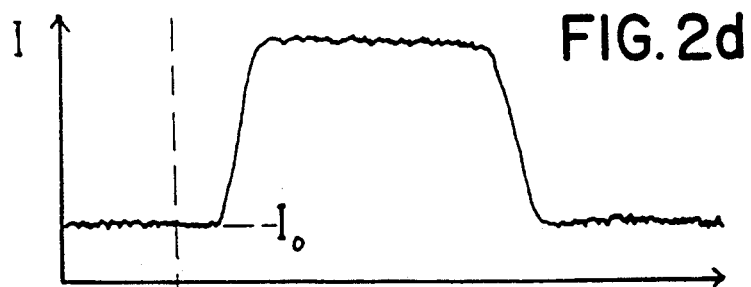
Figure 2E:
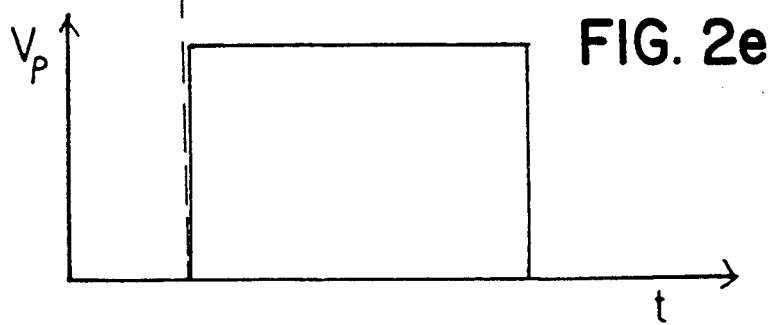

The flow cytometer is depicted schematically in FIG. 1. The optical configuration of different flow cytometers may differ significantly. FIG. 1 encompasses the general features which are required for the present invention. The light from the excitation light source 1 is concentrated on an aperture 6 by a collector lens 3 and again in the excitation focus 2, through which the stream of cells is flowing, by means of suitable lenses 4 and 5. An interference filter 7 selects the particular wavelength band that is required to excite the fluorescence of the cells. The fluorescence and light, scattering produced by the cells as they pass through the excitation focus 2 are collected by a lens 8 which forms an image of the cells on an aperture 9. Behind the aperture 9 is a dichroic mirror 10 and a band filter 11 which separate the scattered light from the fluorescence, which is always of a higher wavelength, and dichroic mirrors 13 and band filters 14 which separate the various spectral components of the fluorescence, so that the scattered light and said fluorescence components can be measured by separate light detectors 12, 15. The signal from each detector is passed through pulse amplifiers 16 into peak-hold circuits 20. The signal from each peak-hold circuit is digitized in analog-to-digital converters 21 which output into a computer 28. The computer stores the data and present them as histograms. The signal from one of the detectors, preferably the light, scattering detector 12 is passed through a pulse height discriminator 19.

Reference should now also be made to FIG. 2. Typically, each cell passes through the excitation focus in the course of some microseconds. When a cell enters the excitation focus 2, the signal from the light detector 12 will begin to increase. When this signal $V_1$, has passed a given level $V_0$, which we denote the "trigger level", an electrical pulse $V_t$ is released from said pulse height discriminator 19. This pulse $V_t$, is passed to a secondary power supply 18, where it triggers an electrical pulse to the light source 1, so that the intensity of the light source increases rapidly, thereby exposing the cell to this increased intensity. The secondary power supply 18 is connected to the light source 1 in parallel with the primary power supply 22 which is feeding the constant operating power to the light source.

In FIG. 2 is depicted the time course of the signal $V_1$ (FIG. 2a), the pulse $V_t$ (FIG. 2b) which triggers the secondary power supply 18, the pulse of electrical power $i_p$ (FIG. 2c) from the secondary power supply 18, and the light pulse I (FIG. 2d), which adds to the constant light intensity $I_0$. The trigger pulse $V_t$ has a duration which is approximately the same as the time required for the cell to pass through the excitation focus 2.

The secondary power supply 18 has a trigger circuit which delivers a voltage pulse $V_p$ (FIG. 2e) to the peak hold circuits 20 of the analog-to-digital converters 21 and thereby triggers the recording of the signal from the various detectors 15. Hence, the cell is measured with a significantly larger sensitivity than when the light source 1 running at constant intensity, as it is in other flow cytometers.

In order to avoid overloading of the light source 1 caused by an excessive rate of cells passing through the excitation focus 2 and triggering pulsing of said light source 1, the secondary power supply 18 has a lower limit to the time between two consecutive pulses sent to the excitation light source 1, and therefore a maximum limit to the rate of such pulses. This limit is set so as to avoid that the mean electrical power that is fed to the light source 1 does not exceed the allowed maximum. For example, the time required for a cell to pass through the excitation focus 1 may be 10 $\mu$sec. If the duration of the pulses of electrical power to the excitation, light source 1 is the same and the size of these pulses is 10 times the constant operating power of the excitation light source, a minimum time between two pulses of 1 msec implies that the average power to the light source will not exceed the constant operating power by more than 10%. Hence, if the constant operating power is set 10% below the maximum allowed value, the mean power consumption of the excitation light source will not exceed this maximum. This measuring rate, that is 1,000 cells per second, is fully sufficient in most applications of flow cytometers.

The secondary light source 18 is also equipped with a trigger circuit 23 which outputs power pulses to the lamp at a constant rate independent of any triggering pulse from the discriminator 17. Hence, the signal caused by the light pulses only can be measured independently.

The increase of the output of the excitation light source 1, produced by the power pulse from the secondary power supply 18, also causes a transient increase of the optical background to the detectors 15, which adds to the signal from the cell itself. In order to correct for this increase, a semitransparent mirror 24 deviates a small portion of the excitation light, that is of the order of a few percent, onto a detector 25. The signal from this detector 25, which is proportional to the optical background, is passed through an electronic amplifier 17, a peak hold circuit 26 and an analog-to-digital converter 27 to the computer 28. In the software of the computer the signal from the detector 25 is subtracted from the signals from the detectors 15 after multiplication with a constant factor, so that the resulting signal is corrected for the transient increase in the optical background.

Having described our invention, we claim:

1. A method for increasing the excitation intensity of a flow cytometer, said cytometer having an excitation light source focus, comprising: receiving a signal produced by a cell entering said focus of said flow cytometer excitation light source, and triggering a pulse of electrical power from a secondary power source to said excitation light source in response to said receiving of said signal to transiently increase the excitation intensity during the time said cell passes through said focus, and thereby produce an increase of measuring sensitivity of said flow cytometer.

2. A method of claim 1, wherein:
  a) said excitation light source is operated at a constant power delivered by an electrical power supply;
  b) and wherein said step of receiving a signal comprises receiving an initial part of a signal from a light signal detector of said flow cytometer and said step of triggering comprises releasing a trigger pulse from a pulse height discriminator in response to said receiving said initial part of said signal, said trigger pulse causing said secondary electrical power supply of said excitation light source to deliver said pulse of electrical power, said pulse of electrical power having a duration similar to the time required for the cell to pass through said focus; and
  c) further comprising, when the secondary power supply delivers said pulse of electrical power to said excitation light source, the step of delivering a simultaneous voltage pulse to peak hold circuits so as to trigger measurement of signals from detectors of fluorescence and light scattering signals.

3. A method of claim 1, wherein a semitransparent mirror deviates a small fraction of the light from said excitation light source onto a light detector, the signal from which is passed to a computer and therein used to correct the signal produced by said cell for transient increase of intensity in optical background resulting from the transient increase of said excitation light intensity from said excitation light source.

4. A method of claim 1, wherein said secondary power supply has a lower limit of the time between sequential pulses of electrical power to said excitation light source so as to prevent the average power fed to said light source from exceeding an allowable maximum.

5. A method for increasing the excitation intensity of a flow cytometer in which a stream of cells, while flowing through an excitation focus, is illuminated by at least one excitation source capable of causing cells in said stream to fluoresce and scatter light, comprising:
  a) continually operating said at least one excitation source so as to illuminate said stream within said excitation focus at a first, lower level of intensity, while continually sensing whether any cell which will fluoresce or scatter light when so illuminated has entered said excitation focus in said stream;
  b) only when thereby sensing that such a cell has entered said excitation focus in said stream, temporarily operating said at least one excitation source so as to illuminate said stream within said excitation focus at a second, higher level of intensity while said cell remains in said excitation focus; and c) while said cell is fluorescing and scattering light in said excitation focus as a result of being illuminated at said second, higher level of intensity, measuring at least one spectral component of fluorescence given off by said cell.

6. The method of claim 5, further comprising:
while conducting step (c), also measuring illuminating energy scattered by said cell to each of a plurality of different angles.

* * * * *